(12) United States Patent
Fischer et al.

(10) Patent No.: US 8,841,294 B2
(45) Date of Patent: Sep. 23, 2014

(54) ACTIVE INGREDIENT COMBINATIONS HAVING INSECTICIDAL AND ACARICIDAL PROPERTIES

(75) Inventors: Reiner Fischer, Monheim (DE); Christoph Erdelen, Leichlingen (DE)

(73) Assignee: Bayer Cropscience AG, Monheim (DE)

( * ) Notice: Subject to any disclaimer, the term of this patent is extended or adjusted under 35 U.S.C. 154(b) by 1346 days.

(21) Appl. No.: 11/030,244

(22) Filed: Jan. 6, 2005

(65) Prior Publication Data
US 2005/0187215 A1 Aug. 25, 2005

Related U.S. Application Data

(62) Division of application No. 10/089,989, filed as application No. PCT/EP00/09323 on Sep. 25, 2000, now Pat. No. 6,893,651.

(30) Foreign Application Priority Data

Oct. 7, 1999 (DE) .................................. 199 48 129

(51) Int. Cl.
- *A01N 43/12* (2006.01)
- *A01N 51/00* (2006.01)
- *A01N 47/40* (2006.01)

(52) U.S. Cl.
CPC ...................................... *A01N 43/12* (2013.01)
USPC ........ 514/229.2; 514/241; 514/341; 514/357; 514/462; 514/473; 424/405; 424/406

(58) Field of Classification Search
USPC ............... 424/405, 406; 514/229.2, 241, 357, 514/341, 473
See application file for complete search history.

(56) References Cited

U.S. PATENT DOCUMENTS

| | | | |
|---|---|---|---|
| 4,531,002 A | 7/1985 | Harris | 544/54 |
| 4,590,272 A | 5/1986 | Shiokawa et al. | 544/335 |
| 4,606,862 A | 8/1986 | Harris | 260/402.5 |
| 4,647,570 A | 3/1987 | Shiokawa et al. | 514/341 |
| 4,678,795 A | 7/1987 | Shiokawa et al. | 514/341 |
| 4,680,294 A | 7/1987 | Shiokawa et al. | 514/256 |
| 4,687,845 A | 8/1987 | Hollowood et al. | 544/54 |
| 4,742,060 A | 5/1988 | Shiokawa et al. | 514/252 |
| 4,772,620 A | 9/1988 | Shiokawa et al. | 514/341 |
| 4,774,247 A | 9/1988 | Shiokawa et al. | 514/256 |
| 4,803,277 A | 2/1989 | Shiokawa et al. | 514/332 |
| 4,806,553 A | 2/1989 | Shiokawa et al. | 514/332 |
| 4,812,454 A | 3/1989 | Shiokawa et al. | 514/256 |
| 4,812,571 A | 3/1989 | Shiokawa et al. | 546/296 |
| 4,845,106 A | 7/1989 | Shiokawa et al. | 514/342 |
| 4,849,432 A | 7/1989 | Shiokawa et al. | 514/341 |
| 4,882,344 A | 11/1989 | Shiokawa et al. | 514/342 |
| 4,914,113 A | 4/1990 | Shiokawa et al. | 514/333 |
| 4,918,086 A | 4/1990 | Gsell | 514/351 |
| 4,918,088 A | 4/1990 | Gsell | 514/357 |
| 4,948,798 A | 8/1990 | Gsell | 514/275 |
| 4,963,572 A | 10/1990 | Gsell | 514/357 |
| 4,963,574 A | 10/1990 | Bachmann et al. | 514/357 |
| 4,988,712 A | 1/1991 | Shiokawa et al. | 514/340 |
| 5,001,138 A | 3/1991 | Shiokawa et al. | 514/342 |
| 5,032,589 A | 7/1991 | Shiokawa et al. | 514/245 |
| 5,034,404 A | 7/1991 | Uneme et al. | 514/365 |
| 5,034,524 A | 7/1991 | Shiokawa et al. | 544/124 |
| 5,039,686 A | 8/1991 | Davies et al. | 514/341 |
| 5,049,571 A | 9/1991 | Gsell | 514/345 |
| 5,051,434 A | 9/1991 | Kozo et al. | 514/357 |
| 5,063,236 A | 11/1991 | Gsell | 514/318 |
| 5,066,808 A | 11/1991 | Shiokawa et al. | 514/231.5 |
| 5,084,467 A | 1/1992 | Shiokawa et al. | 514/357 |
| 5,166,164 A * | 11/1992 | Nanjo et al. | 514/357 |
| 5,175,301 A | 12/1992 | Minamida et al. | 546/272 |
| 5,180,833 A * | 1/1993 | Uneme et al. | 548/202 |
| 5,192,778 A | 3/1993 | Kodaka et al. | 514/341 |
| 5,204,359 A | 4/1993 | Shiokawa et al. | 514/332 |
| 5,204,360 A | 4/1993 | Shiokawa et al. | 514/342 |
| 5,214,152 A | 5/1993 | Minamida et al. | 548/181 |
| 5,238,949 A | 8/1993 | Shiokawa et al. | 514/327 |
| 5,256,679 A | 10/1993 | Minamida et al. | 514/357 |
| 5,262,383 A * | 11/1993 | Fischer et al. | 504/195 |
| 5,264,584 A | 11/1993 | Kodaka et al. | 548/332.5 |
| 5,280,123 A | 1/1994 | Nanjo et al. | 548/111 |
| 5,298,507 A | 3/1994 | Shiokawa et al. | 514/256 |
| 5,304,566 A * | 4/1994 | Ishimitsu et al. | 514/357 |
| 5,384,324 A | 1/1995 | Shiokawa et al. | 514/365 |
| 5,405,961 A | 4/1995 | Nanjo et al. | 544/243 |
| 5,428,032 A | 6/1995 | Shiokawa et al. | 514/226.8 |
| 5,434,181 A | 7/1995 | Kodaka et al. | 514/471 |
| 5,461,167 A | 10/1995 | Shiokawa et al. | 548/202 |
| 5,489,603 A | 2/1996 | Uneme et al. | 514/365 |

(Continued)

FOREIGN PATENT DOCUMENTS

| | | |
|---|---|---|
| BR | 9609100 | 2/1999 |
| CA | 2052731 | 4/1992 |

(Continued)

OTHER PUBLICATIONS

Fisher, Reiner et al.*
Senn Robert et al.*
Uneme, Hideki et al.*
Ishimitsu, Keiichi et al.*
Weeds, 15, (month unavailable) 1967, pp. 20-22, "Calculating Synergistic and Antagonistic Responses of Herbicide Combinations" by S. R. Colby.
Japanese Office Action dispatched Nov. 9, 2010.

*Primary Examiner* — Sabiha N Qazi

(74) *Attorney, Agent, or Firm* — Miles & Stockbridge P.C.

(57) ABSTRACT

The invention relates to insecticidal and acaricidal mixtures comprising certain cyclic ketoenols and agonists or antagonists of nicotinic acetylcholine receptors for protecting plants against attack by pests.

13 Claims, No Drawings

(56) References Cited

U.S. PATENT DOCUMENTS

| | | | |
|---|---|---|---|
| 5,532,365 A | 7/1996 | Kodaka et al. | 544/212 |
| 5,580,889 A | 12/1996 | Shiokawa et al. | 514/343 |
| 5,612,358 A | 3/1997 | Ishimitsu et al. | 514/357 |
| 5,614,527 A | 3/1997 | Kinoshita et al. | 514/256 |
| 5,633,375 A | 5/1997 | Uneme et al. | 544/336 |
| 5,719,146 A | 2/1998 | Shiokawa et al. | 514/229.2 |
| RE35,811 E | 5/1998 | Shiokawa et al. | 514/357 |
| 5,750,704 A | 5/1998 | Shiokawa et al. | 546/275.1 |
| 5,849,768 A | 12/1998 | Minamida et al. | 514/357 |
| 5,852,012 A | 12/1998 | Maienfisch et al. | 514/229.2 |
| 5,935,981 A | 8/1999 | Minamida et al. | 514/365 |
| 5,994,274 A * | 11/1999 | Fischer et al. | 504/282 |
| 6,022,871 A | 2/2000 | Maienfisch et al. | 514/229.2 |
| 6,022,967 A | 2/2000 | Shiokawa et al. | 544/298 |
| 6,160,126 A | 12/2000 | Kando et al. | 548/477 |
| 6,187,773 B1 | 2/2001 | Wu et al. | 514/245 |
| 6,232,309 B1 | 5/2001 | Shiokawa et al. | 514/222.5 |
| 6,297,374 B1 | 10/2001 | Shiokawa et al. | 544/55 |
| 6,344,453 B1 | 2/2002 | Shiokawa et al. | 514/223.8 |
| 6,376,487 B1 | 4/2002 | Maienfisch et al. | 514/229.2 |
| 6,444,690 B2 | 9/2002 | Erdelen et al. | |
| 6,716,442 B2 | 4/2004 | Hunter et al. | |
| 6,716,874 B1 * | 4/2004 | Bretschneider et al. | 514/461 |
| 6,867,169 B1 * | 3/2005 | Senn et al. | 504/132 |
| 6,893,651 B1 * | 5/2005 | Fischer et al. | 424/406 |
| 6,900,190 B2 * | 5/2005 | Fischer et al. | 514/89 |
| 6,919,090 B2 * | 7/2005 | Fischer et al. | 424/406 |
| 7,060,692 B2 * | 6/2006 | Fischer et al. | 514/89 |
| 7,205,289 B2 * | 4/2007 | Fischer et al. | 514/183 |
| 2001/0046994 A1 | 11/2001 | Wu et al. | 514/241 |

FOREIGN PATENT DOCUMENTS

| | | |
|---|---|---|
| EP | 0 528 156 | 2/1993 |
| JP | 63-287764 | 11/1988 |
| JP | 63-307857 | 12/1988 |
| JP | 2-207083 | 8/1990 |
| JP | 3-220176 | 9/1991 |
| JP | 3-246283 | 11/1991 |
| JP | 3-255072 | 11/1991 |
| JP | 3-279359 | 12/1991 |
| JP | 4-9371 | 1/1992 |
| JP | 5-178833 | 7/1993 |
| JP | 5-294953 | 11/1993 |
| JP | 7-173157 | 7/1995 |
| JP | 8-291171 | 11/1996 |
| JP | 11-505813 | 5/1999 |
| JP | 11-508880 | 8/1999 |
| WO | 91/17659 | 11/1991 |
| WO | 9637105 | 11/1996 |
| WO | 9701535 | 1/1997 |

* cited by examiner

ACTIVE INGREDIENT COMBINATIONS HAVING INSECTICIDAL AND ACARICIDAL PROPERTIES

This application is a divisional patent application of U.S. patent application Ser. No. 10/089,989, filed Apr. 2, 2002 and now U.S. Pat. No. 6,893,651, which in turn was the national stage of PCT Application No. PCT/EP00/09323 filed Sep. 25, 2000, which in turn claimed priority of German Patent Application Serial No. 199 48 129.6 filed Oct. 7, 1999.

The present invention relates to novel active compound combinations comprising, on the one hand, a known cyclic ketoenol and, on the other hand, further known insecticidally active compounds, which combinations have very good insecticidal and acaricidal properties.

It is already known that certain cyclic ketoenols can be employed for controlling animal pests such as insects and undesirable acarids (cf. EP-A-528 156). The activity of these substances is good, but sometimes unsatisfactory at low application rates.

Furthermore, it is also known that agonists and antagonists of nicotinic acetylcholine receptors can be used for controlling insects.

It has now been found that mixtures of cyclic ketoenols of the formula (I)

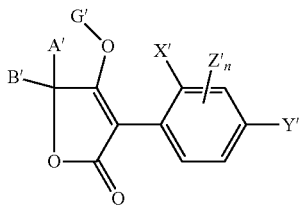

in which

X' represents $C_1$-$C_6$-alkyl, halogen, $C_1$-$C_6$-alkoxy or $C_1$-$C_3$-halogenoalkyl, Y' represents hydrogen, $C_1$-$C_6$-alkyl, halogen, $C_1$-$C_6$-alkoxy, $C_1$-$C_3$-halogenoalkyl, Z' represents $C_1$-$C_6$-alkyl, halogen, $C_1$-$C_6$-alkoxy, n represents a number from 0 to 3, A' and B' are identical or different and each represents hydrogen or in each case optionally halogen-substituted straight-chain or branched $C_1$-$C_{12}$-alkyl, $C_3$-$C_8$-alkenyl, $C_3$-$C_8$-alkinyl, $C_1$-$C_{10}$-alkoxy-$C_2$-$C_8$-alkyl, $C_1$-$C_8$-polyalkoxy-$C_2$-$C_8$-alkyl, $C_1$-$C_{10}$-alkylthio-$C_2$-$C_8$-alkyl, cycloalkyl having 3-8 ring atoms which may be interrupted by oxygen and/or sulphur and in each case optionally halogen-, $C_1$-$C_6$-alkyl-, $C_1$-$C_6$-halogenoalkyl-, $C_1$-$C_6$-alkoxy-, $C_1$-$C_6$-halogenoalkoxy- and/or nitro-substituted phenyl or phenyl-$C_1$-$C_6$-alkyl, or in which A' and B' together with the carbon atom to which they are attached form a saturated or unsaturated 3- to 8-membered ring which is optionally interrupted by oxygen and/or sulphur and is optionally substituted by halogen, $C_1$-$C_6$-alkyl, $C_1$-$C_6$-alkoxy, $C_1$-$C_4$-halogenoalkyl, $C_1$-$C_4$-halogenoalkoxy, $C_1$-$C_4$-alkylthio or optionally substituted phenyl or is optionally benzo-fused, G' represents hydrogen (a) or represents the groups

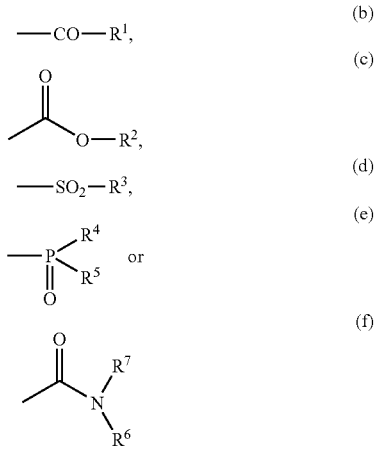

in which $R^1$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl, $C_1$-$C_8$-alkylthio-$C_2$-$C_8$-alkyl, $C_1$-$C_8$-polyalkoxy-$C_2$-$C_8$-alkyl or cycloalkyl having 3-8 ring members which may be interrupted by oxygen and/or sulphur atoms,
represents optionally halogen-, nitro-, $C_1$-$C_6$-alkyl-, $C_1$-$C_6$-alkoxy-, $C_1$-$C_6$-halogenoalkyl- and/or $C_1$-$C_6$-halogenoalkoxy-substituted phenyl;
represents optionally halogen-, $C_1$-$C_6$-alkyl-, $C_1$-$C_6$-alkoxy-, $C_1$-$C_6$-halogenoalkyl- and/or $C_1$-$C_6$-halogenoalkoxy-substituted phenyl-$C_1$-$C_6$-alkyl,
represents in each case optionally halogen- and/or $C_1$-$C_6$-alkyl-substituted pyridyl, pyrimidyl, thiazolyl and pyrazolyl,
or represents optionally halogen- and/or $C_1$-$C_6$-alkyl-substituted phenoxy-$C_1$-$C_6$-alkyl, $R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl, $C_1$-$C_8$-polyalkoxy-$C_2$-$C_8$-alkyl,
represents in each case optionally halogen-, nitro-, $C_1$-$C_6$-alkyl, $C_1$-$C_6$-alkoxy- and/or $C_1$-$C_6$-halogenoalkyl-substituted phenyl or benzyl, $R^3$, $R^4$ and $R^5$ independently of one another each represent in each case optionally halogen-substituted $C_1$-$C_8$-alkyl, $C_1$-$C_8$-alkoxy, $C_1$-$C_8$-alkylamino, di-($C_1$-$C_8$)-alkylamino, $C_1$-$C_8$-alkylthio, $C_2$-$C_5$-alkenylthio, $C_2$-$C_5$-alkinylthio, $C_3$-$C_7$-cycloalkylthio, represent in each case optionally halogen-, nitro-, cyano-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkyl- and/or $C_1$-$C_4$-halogenoalkyl-substituted phenyl, phenoxy or phenylthio, $R^6$ and $R^7$ independently of one another each represent in each case optionally halogen-substituted $C_1$-$C_{20}$-alkyl, $C_1$-$C_{20}$-alkoxy, $C_2$-$C_8$-alkenyl, $C_1$-$C_{20}$-alkoxy-$C_1$-$C_{20}$-alkyl, represent optionally halogen-, $C_1$-$C_{20}$-halogenoalkyl-, $C_1$-$C_{20}$-alkyl- or $C_1$-$C_{20}$-alkoxy-substituted phenyl, represent optionally halogen-, $C_1$-$C_{20}$-alkyl-, $C_1$-$C_{20}$-halogenoalkyl- or $C_1$-$C_{20}$-alkoxy-substituted benzyl or together represent a $C_2$-$C_6$-alkylene ring which is optionally interrupted by oxygen, and at least one acetylcholine receptor agonist or antagonist of the formula (II) are synergistically active and suitable for controlling animal pests. Owing to this synergism, it is possible to use considerably lower amounts of active compound, i.e. the activity of the mixture is higher than the activity of the individual components.

Preference is given to mixtures comprising compounds of the formula (I)
in which
X' represents $C_1$-$C_4$-alkyl, halogen, $C_1$-$C_4$-alkoxy or $C_1$-$C_2$-halogenoalkyl,
Y' represents hydrogen, $C_1$-$C_4$-alkyl, halogen, $C_1$-$C_4$-alkoxy, $C_1$-$C_2$-halo-genoalkyl,
Z' represents $C_1$-$C_4$-alkyl, halogen, $C_1$-$C_4$-alkoxy,
n represents 0 or 1,
A' and B' together with the carbon atom to which they are attached form a saturated 5- to 6-membered ring which is optionally substituted by $C_1$-$C_4$-alkyl and/or $C_1$-$C_4$-alkoxy,
G' represents hydrogen (a) or represents the groups

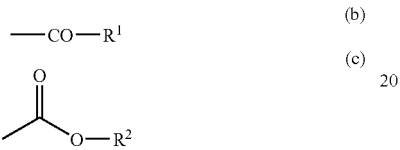

in which
$R^1$ represents in each case optionally halogen-substituted $C_1$-$C_{16}$-alkyl, $C_2$-$C_{16}$-alkenyl, $C_1$-$C_6$-alkoxy-$C_2$-$C_6$-alkyl or cycloalkyl having 3-7 ring atoms which may be interrupted by 1 to 2 oxygen and/or sulphur atoms,
represents optionally halogen-, nitro-, $C_1$-$C_4$-alkyl-, $C_1$-$C_4$-alkoxy-, $C_1$-$C_3$-halogenoalkyl- and/or $C_1$-$C_3$-halogenoalkoxy-substituted phenyl;
$R^2$ represents in each case optionally halogen-substituted $C_1$-$C_{16}$-alkyl, $C_2$-$C_{16}$-alkenyl or $C_1$-$C_6$-alkoxy-$C_2$-$C_6$-alkyl,
represents in each optionally halogen-, nitro-, $C_1$-$C_4$-alkyl-, $C_1$-$C_4$-alkoxy- and/or $C_1$-$C_4$-halogenoalkyl-substituted phenyl or benzyl,
and at least one acetylcholine receptor agonist or antagonist of the formula (II).

Particular preference is given to mixtures comprising the dihydrofuranone derivative of the formula (Ia)

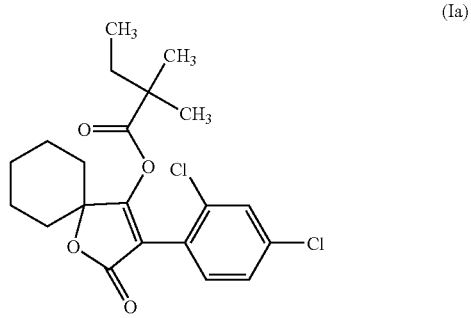 [SMILES: CCC(C)(C)C(=O)OC1=C(c2ccc(Cl)cc2Cl)C(=O)OC12CCCCC2]

and at least one acetylcholine receptor agonist or antagonist of the formula (II).

The agonists and antagonists of the nicotinic acetylcholine receptors are known compounds which are known from the following publications:
European Published Specifications Nos. 464 830, 428 941, 425 978, 386 565, 383 091, 375 907, 364 844, 315 826, 259 738, 254 859, 235 725, 212 600, 192 060, 163 855, 154 178, 136 636, 136 686, 303 570, 302 833, 306 696, 189 972, 455 000, 135 956, 471 372, 302 389, 428 941, 376 279, 493 369, 580 553, 649 845, 685 477, 483 055, 580 553;
German Offenlegungsschriften Nos. 3 639 877, 3 712 307;
Japanese Published Specifications Nos. 03 220 176, 02 207 083, 63 307 857, 63 287 764, 03 246 283, 04 9371, 03 279 359, 03 255 072, 05 178 833, 07 173 157, 08 291 171;
U.S. Pat. Nos. 5,034,524, 4,948,798, 4,918,086, 5,039,686, 5,034,404, 5,532,365;
PCT Applications Nos. WO 91/17 659, 91/4965;
French Application No. 2 611 114;
Brazilian Application No. 88 03 621.

The generic formulae and definitions described in these publications, and also the individual compounds described therein, are expressly incorporated herein by reference.

Some of these compounds are summarized under the term nitromethylenes, nitroimines and related compounds.

Preferably, these compounds can be summarized under the formula (II)

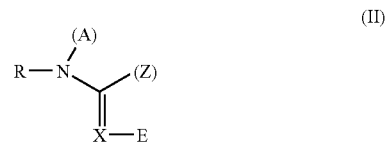

in which
R represents hydrogen or represents optionally substituted radicals selected from the group consisting of acyl, alkyl, aryl, aralkyl, heterocyclyl, heteroaryl and heteroarylalkyl;
A represents a monofunctional group selected from the group consisting of hydrogen, acyl, alkyl, aryl or represents a bifunctional group which is linked to the radical Z;
E represents an electron-withdrawing radical;
X represents the radicals —CH= or =N—, where the radical —CH= may be linked to the radical Z instead of an H atom;
Z represents a monofunctional group selected from the group consisting of alkyl, —O—R, —S—R,

where the radicals R are identical or different and are as defined above,
or represents a bifunctional group which is linked to the radical A or the radical X.

Particular preference is given to compounds of the formula (II) in which the radicals have the following meaning:
R represents hydrogen and represents optionally substituted radicals selected from the group consisting of acyl, alkyl, aryl, aralkyl, heterocyclylalkyl, heteroaryl, heteroarylalkyl.
Examples of acyl radicals are formyl, alkylcarbonyl, arylcarbonyl, alkylsul-phonyl, arylsulphonyl, (alkyl-)-(aryl-)-phosphoryl, which may themselves be substituted.
Examples of alkyl are $C_1$-$C_{10}$-alkyl, in particular $C_1$-$C_4$-alkyl, specifically methyl, ethyl, i-propyl, sec- or t-butyl, which may themselves be substituted.
Examples of aryl are phenyl, naphthyl, in particular phenyl.
Examples of aralkyl are phenylmethyl, phenethyl.

An example of heterocyclylalkyl is the radical

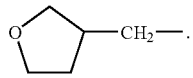

Examples of heteroaryl are heteroaryl having up to 10 ring atoms and N, O, S, in particular N, as heteroatoms. Specific examples are thienyl, furyl, thiazolyl, imidazolyl, pyridyl, benzthiazolyl, pyridazinyl.

Examples of heteroarylalkyl are heteroarylmethyl, heteroarylethyl having up to 6 ring atoms and N, O, S, in particular N, as heteroatoms, in particular optionally substituted heteroaryl as defined under heteroaryl.

Substituents which may be mentioned by way of example and by way of preference are:

alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different, and preferred halogen atoms being fluorine, chlorine or bromine, in particular fluorine, such as trifluoromethyl, hydroxyl; halogen, preferably fluorine, chlorine, bromine and iodine, in particular fluorine, chlorine and bromine, cyano; nitro; amino; monoalkyl- and dialkylamino having preferably 1 to 4, in particular 1 or 2, carbon atoms per alkyl group, such as methylamino, methylethylamino, n-and i-propylamino and methyl-n-butylamino; carboxyl; carbalkoxy having preferably 2 to 4, in particular 2 or 3, carbon atoms, such as carbomethoxy and carboethoxy; sulpho (—SO$_3$H); alkylsulphonyl having preferably 1 to 4, in particular 1 or 2, carbon atoms, such as methylsulphonyl and ethylsulfonyl; arylsulphonyl having preferably 6 or 10 aryl carbon atoms, such as phenylsulphonyl, and also heteroarylamino and heteroarylalkylamino such as chlorpyridylamino and chloropyridylmethylamino.

A represents hydrogen or represents an optionally substituted radical selected from the group consisting of acyl, alkyl, aryl, which are preferably as defined under R, A furthermore represents a bifunctional group. Examples include optionally substituted alkylene having 1 to 4, in particular 1 or 2, C atoms, examples of substituents being the substituents which have been listed further above (and where the alkylene groups may be interrupted by heteroatoms from the group consisting of N, O, S).

A and Z together with the atoms to which they are attached may form a saturated or unsaturated heterocyclic ring. The heterocyclic ring may contain a further 1 or 2 identical or different heteroatoms and/or hetero groups. Preferred heteroatoms are oxygen, sulphur or nitrogen, and preferred hetero groups are N-alkyl, where the alkyl of the N-alkyl group contains preferably 1 to 4, in particular 1 or 2, carbon atoms. Examples of alkyl include methyl, ethyl, n- and i-propyl, and n-, i- and t-butyl. The heterocyclic ring contains 5 to 7, preferably 5 or 6, ring members.

Examples of compounds of the formula (II) in which A and Z together with the atoms to which they are attached form a ring include the following:

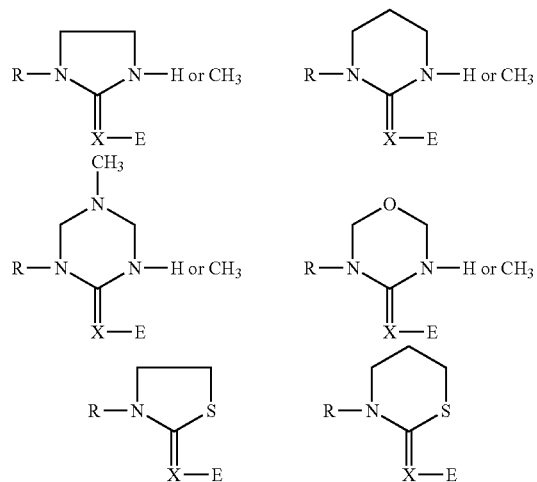

in which

E, R and X are each as defined above and further below.

E represents an electron-withdrawing radical, specific examples being NO$_2$, CN, halogenoalkylcarbonyl, such as halogeno-C$_1$-C$_4$-alkylcarbonyl, for example COCF$_3$, alkylsulphonyl (for example SO$_2$—CH$_3$), halogenoalkylsulphonyl (for example SO$_2$CF$_3$) and with particular preference NO$_2$ or CN.

X represents —CH= or —N=.

Z represents an optionally substituted radical selected from the group consisting of alkyl, —OR, —SR, —NRR, where R and the substituents are preferably as defined above.

Z may, in addition to the ring mentioned above, together with the atom to which it is attached and the radical

instead of X, form a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl or N-alkyl group contains preferably 1 to 4, preferably 1 or 2, carbon atoms. Examples of alkyl include methyl, ethyl, n- and i-propyl and n-, i- and t-butyl. The heterocyclic ring contains 5 to 7, preferably 5 or 6, ring members. Examples of the heterocyclic ring include pyrrolidine, piperidine, piperazine, hexamethyleneimine, morpholine and N-methylpiperazine.

The agonists and antagonists of the nicotinic acetylcholine receptors are particularly preferably compounds of the formula (II) in which R represents

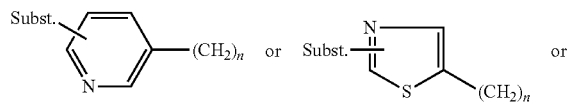

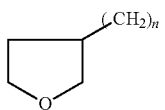
where
n represents 0, 1 or 2, and preferably represents 1,
Subst. represents one of the substituents mentioned above, especially halogen, in particular chlorine, and A, Z, X and E are each as defined above.
R represents in particular
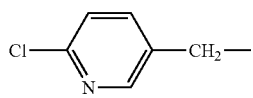 or
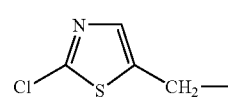 or 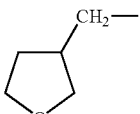.
The following compounds are specific examples:
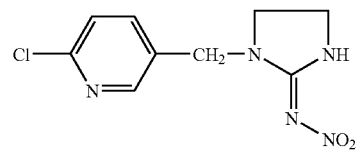
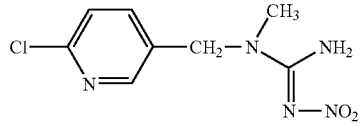
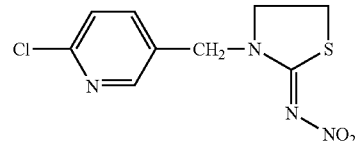
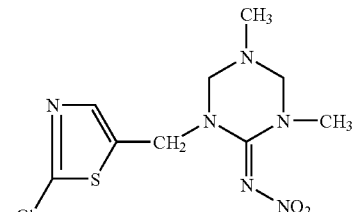
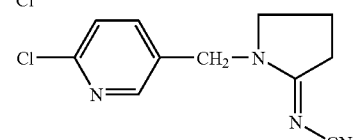
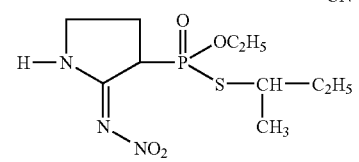
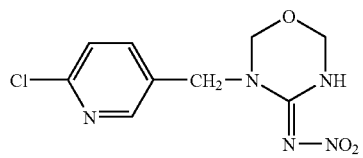
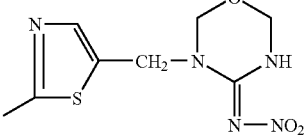
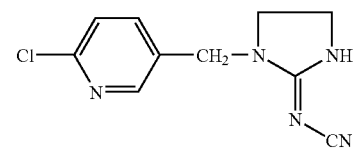
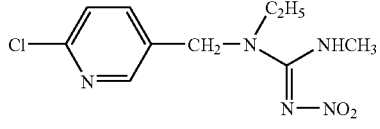
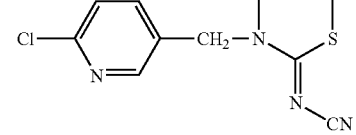
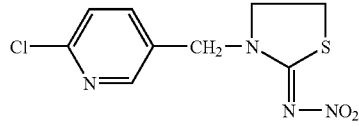
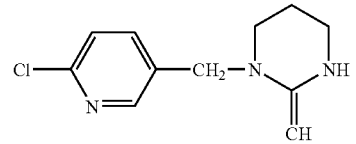
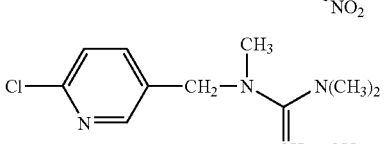
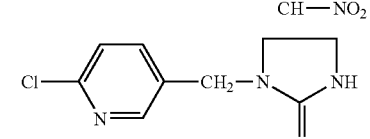
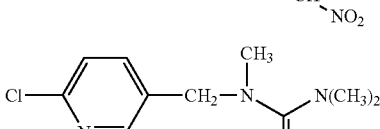
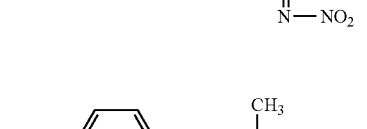

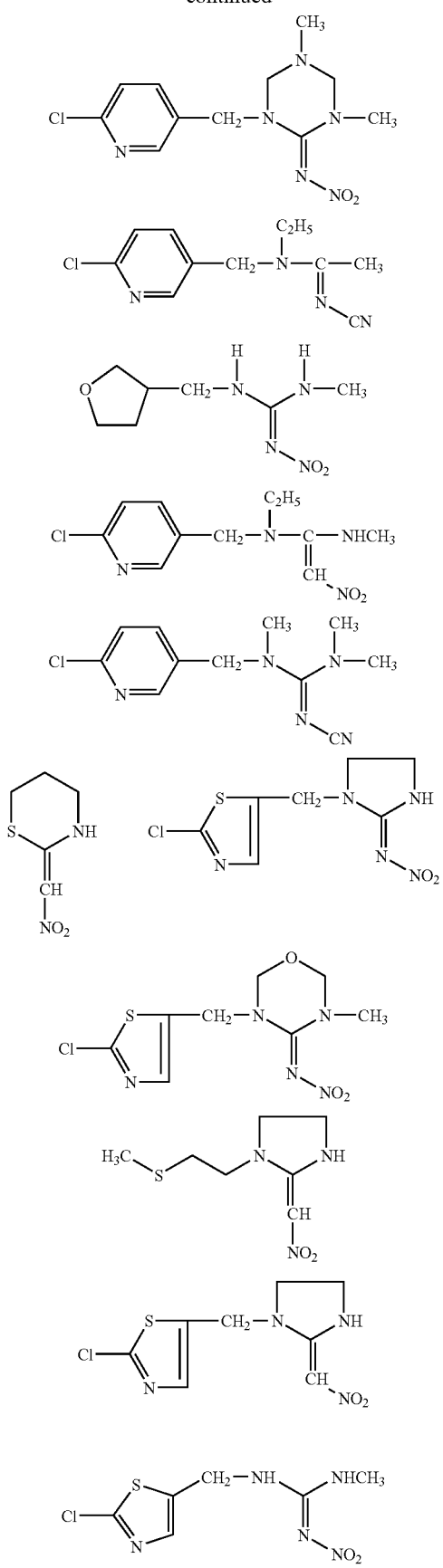
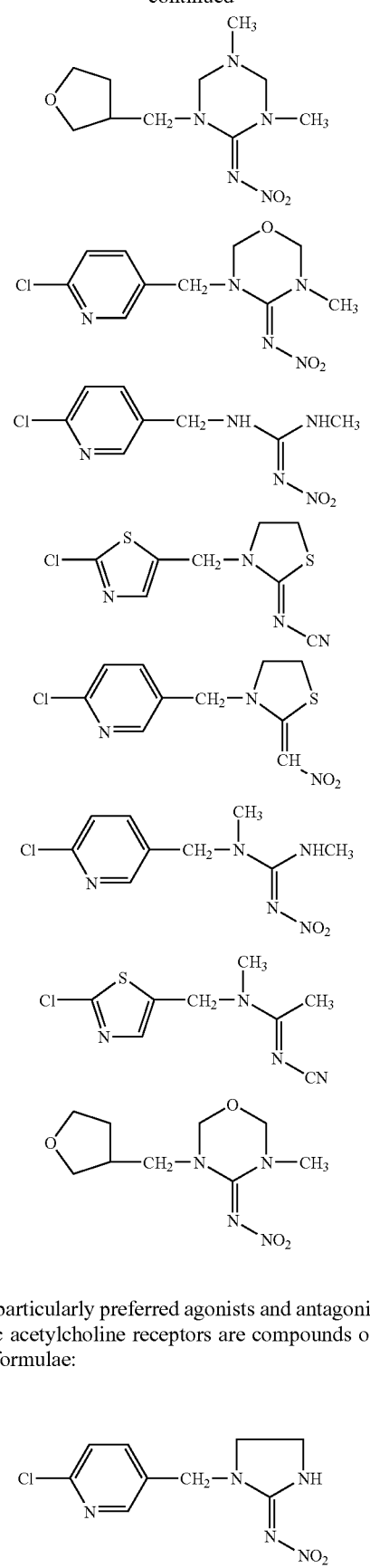
Very particularly preferred agonists and antagonists of the nicotinic acetylcholine receptors are compounds of the following formulae:
(IIa)

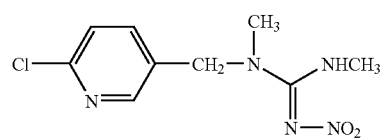
(IIb)
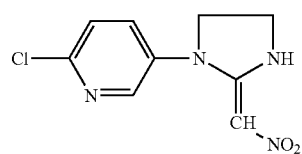
(IIc)
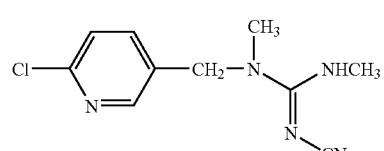
(IId)
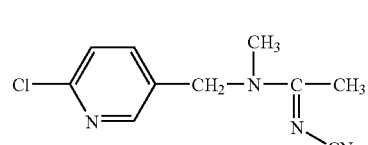
(IIe)
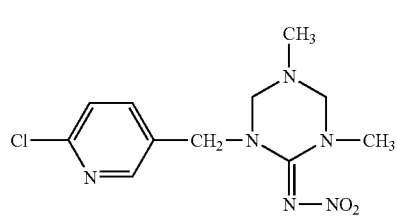
(IIf)
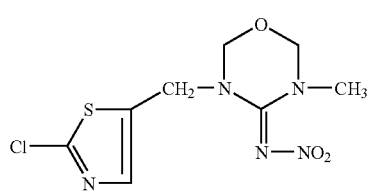
(IIg)
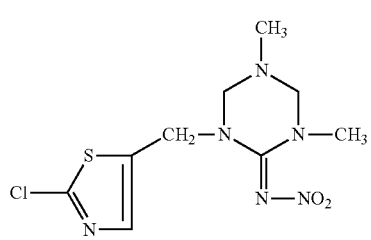
(IIh)
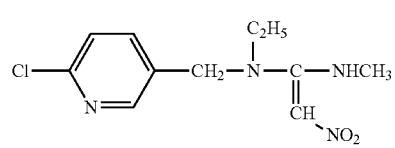
(IIi)
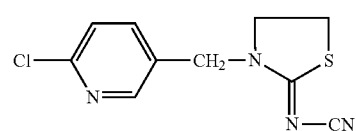
(IIk)
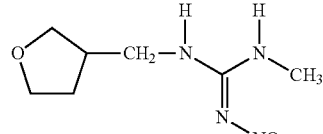
(II l)
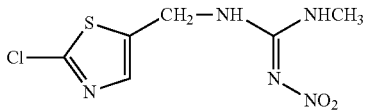
(II m)
in particular a compound of the following formula
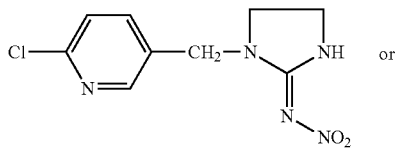
(IIa)
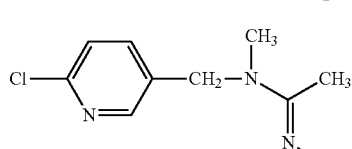
(IIe)
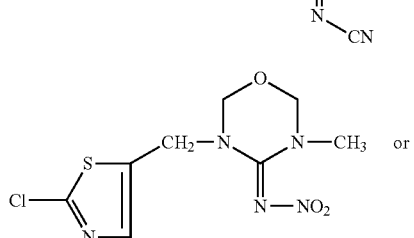
(IIg)
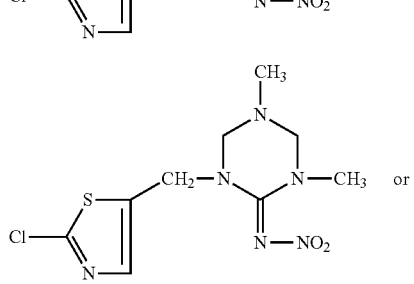
(IIh)
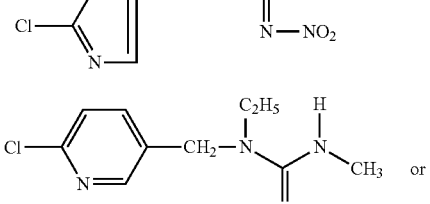
(II i)
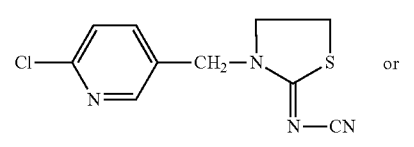
(II k)
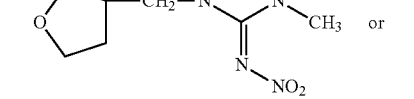
(II l)

$$\text{(II m)}$$

Cl—[thiazole]—CH$_2$—NH—C(NHCH$_3$)=N—NO$_2$

Very particular preference is given to the compounds of the formulae (IIa), (IIk), (IIm).

Furthermore, very particular preference is given to the compounds of the formulae (IIe), (IIg), (IIh), (II 1), (IIc).

A particularly preferred mixture comprises the compound of the formula (Ia) and the compound of the formula (IIa);

a further particularly preferred mixture comprises the compound of the formula (Ia) and the compound of the formula (IIk);

particular preference is furthermore given to mixtures which comprise the compound of the formula (Ia) and the compound of the formula (IIm).

The active compound mixtures are suitable for controlling animal pests, in particular insects, arachnids and nematodes, encountered in agriculture, in forests, in the protection of stored products and in the hygiene sector, and they are tolerated well by plants and have favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus, Gryllotalpa*spp., *Locusta migratoria migratorioides, Melanoplus differentialis* and *Schistocerca gregaria.*

From the order of the Dermaptera, for example, *Forficula auricularia.*

From the order of the Isoptera, for example, *Reticulitermes* spp.

From the order of the Anoplura, for example, *Pediculus humanus corporis, Haematopinus*spp. and *Linognathus* spp.

From the order of the Mallophaga, for example, *Trichodectes* spp. and *Damalinea*spp.

From the order of the Thysanoptera, for example, *Hercinothrips femoralis* and *Thrips tabaci.*

From the order of the Heteroptera, for example, *Eurygaster* spp., *Dysdercus intermedius, Piesma quadrata, Cimex lectularius, Rhodnius prolixus*and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Phylloxera vastatrix, Pemphigus* spp., *Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

From the order of the Siphonaptera, for example, *Xenopsylla cheopis* and *Ceratophyllus* spp.

From the order of the Arachnida, for example, *Scorpio maurus* and *Latrodectus mactans.*

From the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The phytoparasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp., *Trichodorus* spp.

The ratio of the compounds of the formula (I) and the compounds of the formula (II) employed, and the total amount of the mixture, depends on the kind and the occurrence of the pests. For each application, the optimum ratios and overall application rates can be determined in each case by test series. In general, the ratio of the compounds of the formula (I) to the compounds of the formula (II) is from 1:100 to 100:1, preferably from 1:25 to 25:1 and particularly preferably from 1:5 to 5:1. These are parts by weight.

The active compound mixtures according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphoric esters, carbamates, carboxylates, chlorinated hydrocarbons, phenylureas and substances produced by microorganisms. Specifically, the insecticides and fungicides mentioned further above may be mentioned as mixing components.

Insecticides which can be admixed, if appropriate, are, for example:

Phosphoric esters, such as azinphos-ethyl, azinphos-methyl, α-1-(4-chlorophenyl)-4-(O-ethyl, S-propyl)phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulprofos, triazophos and trichlorfon;

carbamates, such as aldicarb, bendiocarb, α-2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds, preferably dimethyl(phenyl)silylmethyl 3-phenoxybenzyl ethers, such as dimethyl-(4-ethoxyphenyl)-silylmethyl 3-phenoxybenzyl ether, or (dimethylphenyl)-silyl-methyl 2-phenoxy-6-pyridylmethyl ethers, such as, for example, dimethyl-(9-ethoxyphenyl)-silylmethyl 2-phenoxy-6-pyridylmethyl ether, or [(phenyl)-3-(3-phenoxyphenyl)-propyl](dimethyl)-silanes, such as, for example, (4-ethoxyphenyl)-[3-(4-fluoro-3-phenoxyphenyl)-propyl]dimethyl-silane, silafluofen; pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl-2,2-dimethyl-3-(2-chloro-2-trifluoro-methylvinyl)cyclopropanecarboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridyl)-methyl]-4,5-dihydro-N-nitro-1H-imidazole-2-amine (imidacloprid), N-[(6-chloro-3-pyridyl)methyl]-N²-cyano-N¹-methylacetamide (NI-25);

abamectin, AC 303.630, acephate, acrinathrin, alanycarb, aldoxycarb, aldrin, amitraz, azamethiphos, Bacillus thuringiensis, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulphuryl fluoride, tar oils, teflubenzuron, tefluthrin, temephos, terbufos, tetrachlorvinphos, tetramethrin, O-2-tert-butyl-pyrimidin-5-yl O-isopropyl phosphorothiate, thiocyclam, thiofanox, thiometon, tralomethrin, triflumuron, trimethacarb, vamidothion, Verticillium lacanii, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alpha-cypermethrin, cyophenothrin, cyromazine, dazomet, DDT, demeton-S-methyl-sulphone, diafenthiuron, dialifos, dicrotophos, diflubenzuron, dinoseb, deoxabenzofos, diaxacarb, disulfoton, DNOC, empenthrin, endosulfan, EPN, esfenvalerate, ethiofencarb, ethion, etofenprox, fenobucarb, fenoxycarb, fensulfothion, spinosynen, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous chloride, metam, Metarthizium anisopliae, methacrifos, methamidophos, methidathion, methiocarb, methoprene, methoxychlor, methyl isothiocyanate, metholcarb, mevinphos, monocrotophos, naled, Neodiprion sertifer NPV, nicotine, ometthoate, oxydemeton-methyl, pentachlorophenol, petroleum oils, phenothrin, phenthoate, phorate.

The further insecticides which can be admixed, if appropriate, can also be from the class of the compounds of the general formula (I).

Preferred fungicides which may be admixed, if appropriate, are:

Triazoles, such as:

azaconazole, propiconazole, tebuconazole, cyproconazole, metaconazole, amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, paclobutrazol, (∀)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

Imidazoles, such as:

imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.

Methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenylsulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethylbenzoyl)pyrrol-1-yl]-3-methoxyacrylate, methyl (E)-2-[2-(3-methoxyphenoxy)phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alphahydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxyphenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenyl]-3-methoxyacrylate, methyl (E)-2-[2-(3-ethoxyphenoxy)phenyl]-3-methoxyacrylate, methyl (E)-2-[2-

(4-tert-butylpyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-(3-methylpyridin-2-yloxymethyl)phenyl]-3-methoxyacrylate, methyl (E)-2-[2-[6-(2-methylphenoxy)pyrimidin-4-yloxy]phenyl]-3-methoxyacrylate, methyl (E)-2-[2-(5-bromopyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethoximinomethyl)phenyl]-3-methoxyacrylate, methyl (E)-2-{2-[6-(6-methylpyridin-2-yloxy)pyrimidin-4-yloxy]phenyl}-3-methoxyacrylate, methyl (E),(E)-2-{2-(3-methoxyphenyl)methyloximinomethyl]phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]phenyl}-3-methoxyacrylate, methyl (E)-2-{2-[6-(2-n-propylphenoxy)-1,3,5-triazin-4-yloxy]phenyl}-3-methoxyacrylate, methyl (E),(E)-2-{2-[(3-nitrophenyl) methyloximinomethyl]phenyl}-3-methoxyacrylate;

succinate dehydrogenase inhibitors such as:

fenfuram, furcarbanil, cyclafluramid, firmecyclox, seedvax, metsulfovax, pyrocarbolid, oxycarboxin, shirlan, mebenil (mepronil), benodanil, flutolanil (Moncut); naphthalene derivatives such as terbinafine, naftifine, butenafine, 3-chloro-7-(2-aza-2,7,7-trimethyl-oct-3-en-5-ine);

sulfenamides, such as dichlofluanid, tolylfluanid, folpet, fluorfolpet; captan, captofol; benzimidazoles, such as carbendazim, benomyl, furathiocarb, fuberidazole, thiophonatmethyl, thiabendazole or their salts;

morpholine derivatives, such as fenpropimorph, falimorph, dimethomorph, dodemorph; aldimorph, fenpropidine and their arylsulphonates, such as, for example, p-toluenesulphonic acid and p-dodecylphenylsulphonic acid;

dithiocarbamates, cufraneb, ferbam, mancopper, mancozeb, maneb, metam, metiram, thiram zeneb, ziram:

benzothiazoles, such as 2-mercaptobenzothiazole;

benzamides, such as 2,6-dichloro-N-(4-trifluoromethylbenzyl)-benzamide;

boron compounds, such as boric acid, boric esters, borax;

formaldehyde and formaldehyde-releasing compounds, such as benzyl alcohol mono(poly)-hemiformal, oxazolidine, hexa-hydro-S-triazines, N-methylolchloroacetamide, paraformadehyde, nitropyrin, oxolinic acid, tecloftalam;

tris-N-(cyclohexyldiazeneiumdioxy)-aluminium, N-(cyclohexyldiazeneiumdioxy)-tributyltin or K salts, bis-N-(cyclohexyldiazeniumdioxy)-copper;

N-methylisothiazolin-3-one, 5-chloro-N-methylisothiazolin-3-one, 4,5-dichloro-N-octylisothiazolin-3-one, N-octyl-isothiazolin-3-one, 4,5-trimethylene-isothiazolinone, 4,5-benzoisothiazolinone, N-methylolchloroacetamide;

aldehydes, such as cinnamaldehyde, formaldehyde, glutaraldehyde, β-bromocinnamaldehyde; thiocyanates, such as thiocyanatomethylthiobenzothiazole, methylenebisthiocyanate, and the like;

quaternary ammonium compounds, such as benzyldimethyltetradecylammonium chloride, benzyldimethyldodecylammonium chloride, didecyldimethylammonium chloride;

iodine derivatives, such as diiodomethyl p-tolyl sulphone, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;

phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts;

microbicides having an activated halogen group, such as chloroacetamide, bronopol, bronidox, tectamer, such as 2-bromo-2-nitro-1,3-propanediol, 2-bromo-4'-hydroxyacetophenone, 2,2-dibromo-3-nitrile-propionamide, 1,2-dibromo-2,4-dicyanobutane, β-bromo-β-nitrostyrene;

pyridines, such as 1-hydroxy-2-pyridinethione (and their Na, Fe, Mn, Zn salts), tetrachloro-4-methylsulphonylpyridine, pyrimethanol, mepanipyrim, dipyrithion, 1-hydroxy-4-methyl-6-(2,4,4-trimethylpentyl)-2(1 H)-pyridine;

metal soaps, such as copper hydroxycarbonate, copper sulphate, copper chloride, tin naphtenate, copper naphtenate, zinc naphtenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;

metal salts, such as copper hydroxycarbonate, sodium dichromate, potassium dichromate, potassium chromate, copper sulphate, copper chloride, copper borate, zinc fluorosilicate, copper fluorosilicate, in particular mixtures with fixing agents; oxides, such as tributyltin oxide, $Cu_2O$, CuO, ZnO;

dialkyldithiocarbamates, such as Na and Zn salts of dialkyldithiocarbamates, tetramethylthiuram disulphide, potassium N-methyl-dithiocarbamate;

nitriles, such as 2,4,5,6-tetrachloroisophthalonitrile, disodium cyano-dithioimidocarbamate;

quinolines, such as 8-hydroxyquinoline, and their Cu salts; mucochloric acid, 5-hydroxy-2(5H)-furanone;

4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxymethyl-N'-methyl-dithiocarbamate, 2-oxo-2-(4-hydroxy-phenyl)acethydroximic acid chloride, phenyl 2-chloro-cyano-vinyl sulphone, phenyl 1,2-dichloro-2-cyano-vinyl sulphone;

Ag, Zn or Cu-containing zeolites, alone or enclosed in polymeric active compounds. or else mixtures of a plurality of the abovementioned fungicides.

The active compound content of the use forms prepared from the commercially available formulations can vary within wide limits. The active compound concentration of the use forms can be from 0.0000001 to 95% by weight of active compound, preferably between 0.0001 and 1% by weight.

The active compound mixtures can be converted into the customary formulations, such as solutions, emulsions, suspensions, powders, foams, pastes, granules, aerosols, active-compound-impregnated natural and synthetic materials, very fine encapsulations in polymeric substances and in coating compositions for seed, furthermore into formulations with smokes, such as fumigating cartridges, fumigating cans, fumigating coils and the like, and also ULV cold mist and warm mist formulations.

These formulations are prepared in a known manner, for example by mixing the active compounds with extenders, that is liquid solvents, pressurized liquefied gases and/or solid carriers, optionally with the use of surfactants, that is emulsifiers and/or dispersing agents, and/or foam-formers. If the extender used is water, it is also possible to use for example organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water; by liquefied gaseous extenders or carriers are meant liquids which are gaseous at ambient temperature and under atmospheric pressure, for example aerosol propellant, such as halogenated hydrocarbons and also butane, propane, nitrogen and carbon dioxide; suitable solid carriers are: for example, ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example, lignin-sulphite waste liquors and methylcellulose.

Tackifiers such as carboxy-methylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 percent by weight of active compound mixture, preferably between 0.5 and 90 percent by weight of active compound mixture.

The mixtures according to the invention can be applied via the leaves.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including transgenic plants and including plant cultivars which can or cannot be protected by plant breeder certificates. Parts of plants are to be understood as meaning all above-ground and below-ground parts and organs of plants, such as shoot, leaf, flower and root, examples which may be mentioned being leaves, needles, stems, trunks, flowers, fruit bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

When using the active compound combinations according to the invention, the application rates can be varied within a relatively wide range, depending on the type of application. In the treatment of parts of plants, the active compound combination application rates are generally between 0.1 and 10,000 g/ha, preferably between 10 and 1000 g/ha.

The good insecticidal and acaricidal action of the active compound combinations according to the invention is evident from the examples below. While the individual active compounds exhibit weaknesses with regard to the activity, the combinations have an activity which exceeds a simple addition of activities.

A synergistic effect of insecticides and acaricides is always present when the activity of the active compound combinations exceeds the total of the activities of the active compounds when applied individually.

The expected activity for a given combination of two active compounds can be calculated as follows (after S. R. Colby, Weeds 15 (1967), 20-22):

If

X is the efficacy when applying the active compound A at an application rate of m g/ha or in a concentration of m ppm, Y is the efficacy when applying the active compound B at an application rate of n g/ha or at a concentration of n ppm and E is the efficacy when applying the active compounds A and B at application rates of m and n g/ha or at a concentration of m and n ppm, then $$E = X + Y - \frac{X \cdot Y}{100}$$

The efficacy is calculated in %. 0% is an efficacy which corresponds to that of the control, whereas an efficacy of 100% means that no infection is observed.

If the actual activity exceeds the calculated value, then the activity of the combination is superadditive, i.e. a synergistic effect exists. In this case, the efficacy which was actually observed must be greater than the value for the expected efficacy (E) calculated from the abovementioned formula.

EXAMPLE A

*Aphis Gossypii* Test

| Solvent: | 3 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentrations.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed. The kill rates that are determined are assessed using Colby's formula.

In this test, for example, the following active compound combination according to the present application exhibits a synergistically enhanced activity compared with the active compounds applied individually:

TABLE A

Sheet 1
plant-damaging insects
*Aphis gossypii* test

| Active compounds | Active compound concentration in ppm | Kill rates in % after $6^d$ | |
|---|---|---|---|
| Ex. (Ia) known | 1.6 | 0 | |
| Ex. (IIa) known | 1.6 | 85 | |
| Ex. (Ia) + Ex. (IIa) | | found* | calc.** |
| according to the invention | 1.6 + 1.6 | 95 | 85 | found* = activity found
calc.** = activity calculated using Colby's formula

TABLE A

Sheet 2
plant-damaging insects
*Aphis gossypii* test

| Active compounds | Active compound concentration in ppm | Kill rate in % after $6^d$ | |
|---|---|---|---|
| Ex. (Ia) known | 1.6 | 0 | |
| Ex. (IIk) known | 1.6 | 55 | |
| Ex. (Ia) + Ex. (IIk) | | found* | calc.** |
| according to the invention | 1.6 + 1.6 | 95 | 55 | found* = activity found
calc.** = activity calculated using Colby's formula

EXAMPLE B

*Aphis Gossypii* Test/Larval Mortality

| Solvent: | 3 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentrations.

Cotton leaves (*Gossypium hirsutum*) which are heavily infested by adults and larvae of the cotton aphid (*Aphis gossypii*) are treated by being dipped into the preparation of active compound of the desired concentration.

After the desired period of time, the kill of larvae in % is determined. 100% means that all larvae have been killed; 0% means that none of the larvae have been killed. The kill rates that are determined are assessed using Colby's formula.

In this test, for example, the following active compound combination according to the present application exhibits a synergistically enhanced activity compared with the active compounds applied individually:

TABLE B

Sheet 1
plant-damaging insects
*Aphis gossypii* test/larval mortality

| Active compounds | Active compound concentration in ppm | Kill rate in % after $6^d$ | |
|---|---|---|---|
| Ex. (Ia) known | 1.6 | 0 | |
| Ex. (IIa) known | 1.6 | 80 | |
| Ex. (Ia) + Ex. (IIa) | | found* | calc.** |
| According to the invention | 1.6 + 1.6 | 95 | 80 | found* = activity found
calc.** = activity calculated using Colby's formula

TABLE B

Sheet 2
plant-damaging insects
*Aphis gossypii* test/larval mortality

| Active compounds | Active compound concentration in ppm | Kill rate in % after $6^d$ | |
|---|---|---|---|
| Ex. (Ia) Known | 1.6 | 0 | |
| Ex. (IIk) Known | 1.6 | 60 | |
| Ex. (Ia) + Ex. (IIk) | | found* | calc.** |
| according to the invention | 1.6 + 1.6 | 95 | 60 | found* = activity found
calc.** = activity calculated using Colby's formula

EXAMPLE C

*Myzus* Test

| Solvent: | 3 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentrations.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all animals have been killed; 0% means that none of the animals have been killed. The kill rates determined are assessed using Colby's formula.

In this test, for example, the following active compound combination according to the present application exhibits a synergistically enhanced activity compared with the active compounds applied individually:

TABLE C

| | plant-damaging insects *Myzus* test | |
|---|---|---|
| Active compounds | Active compound concentration in ppm | Kill rates in % after $1^d$ |
| Ex. (Ia) Known | 1.6 | 0 |
| Ex. (IIa) Known | 1.6 | 70 |
| Ex. (Ia) + Ex. (IIa) | | found*  calc.** |
| according to the invention | 1.6 + 1.6 | 98       70 | found* = activity found
calc.** = activity calculated using Colby's formula

EXAMPLE D

*Myzus* Test/Larval Mortality

| Solvent: | 3 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentrations.

Cabbage leaves (*Brassica oleracea*) which are heavily infested by adults and larvae of the peach aphid (*Myzus persicae*) are treated by being dipped into the preparation of active compound of the desired concentration.

After the desired period of time, the kill of the larvae in % is determined. 100% means that all larvae have been killed; 0% means that none of the larvae have been killed. The kill rates determined are assessed using Colby's formula.

In this test, for example, the following active compound combination according to the present application exhibits a synergistically enhanced activity compared with the active compounds applied individually:

TABLE D

| | plant-damaging insects Myzus test/larval mortality | |
|---|---|---|
| Active compounds | Active compound concentration in ppm | Kill rates in % after $1^d$ |
| Ex. (Ia) Known | 0.32 | 0 |
| Ex. (IIa) Known | 0.32 | 0 |
| Ex. (Ia) + Ex. (IIa) according to the invention | 0.32 + 0.32 | found*  calc.** 55       0 | found* = activity found
calc.** = activity calculated using Colby's formula

The invention claimed is:

1. A composition, comprising a synergistically effective mixture of:
   a) a cyclic ketoenol compound of the Formula (Ia)

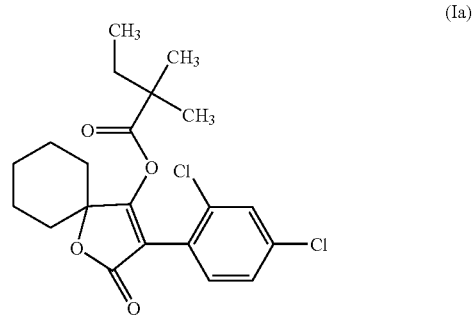 [SMILES: CCC(C)(C)C(=O)OC1=C(c2ccc(Cl)cc2Cl)C(=O)OC12CCCCC2]

and
   b) a member selected from the group consisting of one or more agonists of nicotinic acetylcholine receptors and one or more antagonists of nicotinic acetylcholine receptors, which agonist or antagonist is a compound of the formula

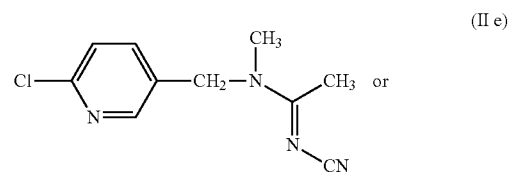

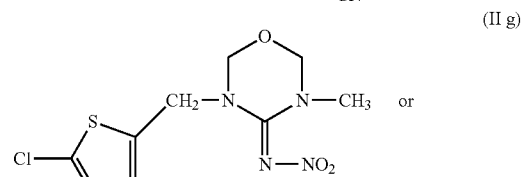

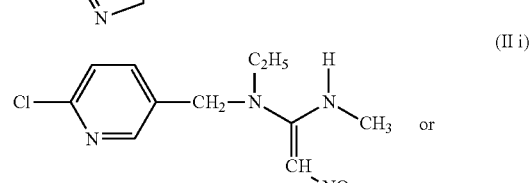

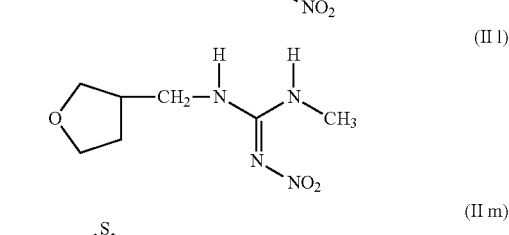

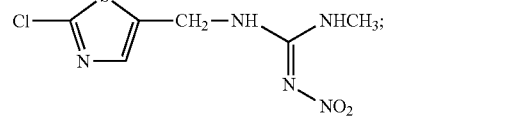

wherein said cyclic ketoenol compound and either said agonist or said antagonist of nicotinic acetylcholine receptors, respectively, are present in a ratio of from 1:25 to 25:1.

2. A method for controlling animal pests selected from the group consisting of insects, arachnids, nematodes and combinations thereof comprising the step of applying the composition of claim 1 to a member selected from the group consisting of a habitat of said animal pests, said animal pests and combinations thereof.

3. A process for preparing a pesticide comprising the step of mixing:

a) the composition according to claim 1 with b) a member selected from the group consisting of an extender, a surfactant, and combinations thereof.

4. A method for controlling sucking insect pests in or on crop plants by applying a composition as described in claim 1 to the crop plant, the habitat from which it grows or combinations thereof.

5. The method of claim 4 wherein the sucking insect is a pest of the order Homoptera.

6. The method of claim 5 wherein the sucking pest is *Aphis gossipyii* or *Myzus persicae*.

7. The composition of claim 1, wherein b) is a compound of Formula (II e)

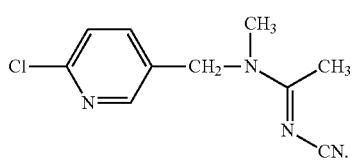

8. The composition of claim 1, wherein b) is a compound of Formula (II g)

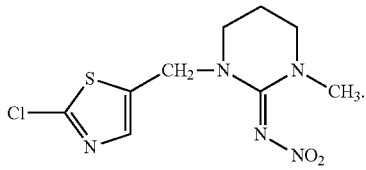

9. The composition of claim 1, wherein b) is a compound of the Formula (II i)

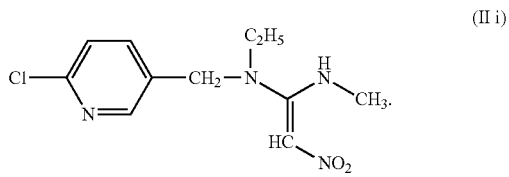 [SMILES: CCN(Cc1ccc(Cl)nc1)/C(=C/[N+](=O)[O-])NC]

10. The composition of claim 1, wherein b) is a compound of the Formula (II l)

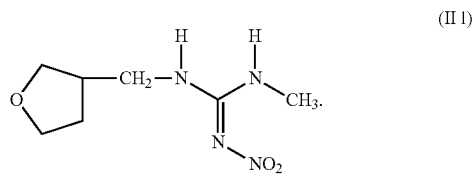 [SMILES: CN/C(=N\[N+](=O)[O-])NCC1CCOC1]

11. The composition of claim 1, wherein b) is a compound of the Formula (II m)

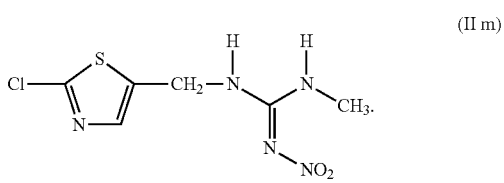 [SMILES: CN/C(=N\[N+](=O)[O-])NCc1cnc(Cl)s1]

12. A composition according to claim 1, wherein said cyclic ketoenol compound and either said agonist or said antagonist of nicotinic acetylcholine receptors, respectively, are present in a ratio of from 1:5 to 5:1.

13. A composition according to claim 1, wherein said cyclic ketoenol compound and either said agonist or said antagonist of nicotinic acetylcholine receptors, respectively, are present in a ratio of from 1:1 to 1:1.

* * * * *